US006221848B1

(12) United States Patent
Greenberger

(10) Patent No.: US 6,221,848 B1
(45) Date of Patent: Apr. 24, 2001

(54) PROTECTION OF THE ESOPHAGUS FROM CHEMOTHERAPEUTIC OR IRRADIATION DAMAGE BY GENE THERAPY

(75) Inventor: Joel S. Greenberger, Sewickley, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/075,532

(22) Filed: May 11, 1998

(51) Int. Cl.$^7$ .......................... A01N 43/04; A01N 63/00; C12N 15/00; C12N 15/63; C07G 17/00

(52) U.S. Cl. .......................... 514/44; 435/320.1; 435/455; 435/267; 424/93.2; 424/93.21

(58) Field of Search .................................. 435/267, 320.1; 424/93.2, 172.1, 93.21; 514/44

(56) References Cited

U.S. PATENT DOCUMENTS

| 4,980,286 | 12/1990 | Morgan et al. | 435/371 |
|---|---|---|---|
| 5,240,847 | 8/1993 | Heckl et al. | 435/189 |
| 5,599,712 | * 2/1997 | Greenberger | 435/267 |

FOREIGN PATENT DOCUMENTS

| 93/12756 | 7/1993 | (WO) . |
|---|---|---|
| WO 94/19493 | * 9/1994 | (WO) . |
| WO 94/21283 | 9/1994 | (WO) . |
| WO 98/00160 | * 1/1998 | (WO) . |

OTHER PUBLICATIONS

Mastrangelo et al., Seminars in Oncology, vol. 23, No. 1, pp. 4–21, Feb. 1996.*
Orkin et al., Report and Recommendations for the Panel to Assess the NIH Investment in Research on Gene Therapy, Dec. 1995.*
Epperly et al. "Prevention of late effects of irradiation lung damage by Manganese superoxide dismutase gene therapy" Gene Therapy, (1998 Feb) 5 (2) 196–208.
Epperly et al. "Protection of the lung from ionizing irradiation damage by inhalation gene therapy" International Journal of Radiation Oncology Biology Physics, (1995), vol. 32, No. Supp. 1 pp. 173.
Zwacka et al. "Redox gene therapy protects human IB–3 lung epithelial cells against ionizing radiation–induced apoptosis" Human Gene Therapy, (Jun. 10, 1998) 9 (9) 1381–6.
Epperly et al. "Intratracheal injection of adenovirus containing the human MnSOD transgene protects athymic nude mice from irradiation–induced organizing alveolitis." International Journal of Radiation Oncology, Biology, Physics, (Jan. 1, 1999) 43 (1) 169–81.
Stickle et al. "Prevention of irradiation–induced esophagitis by plasmid/liposome delivery of the human manganese superoxide dismutase transgene." Radiation Oncology Investigations, (1999) 7/4 (204–217.

Mastrangelo et al., Seminars in Oncology vol. 23 (1), pp. 4–21 (no year).
Orkin et al., Report and Recommendations of the Panel to Assess the NIH investment in Research on Gene Therapy (no year).
Alton et al., Nature Genetics, 5:135–142, 1993.
Hockenberry et al., Cell, 75: 241–251, 1993.
Jaffe et al., Nature Genetics, 1: 372–378, 1992.
Jolly, Cancer Gene Therapy, 1(1): 51–64, 1994.
Mulligan, Science, 260:926–932, 1993.
Petkau, Cancer Treatment Rev., 13: 17–44, 1986.
Sorrentino et al., Science, 257: 99–103, 1992.
Wu et al., J. Biol. Chem., 263: 14621–14624, 1988.
Ledley, F.D., Human Gene Therapy, 2: 77–83 (1991).
Ledley, F.D., Current Opinion in Biotechnology, 5: 626–636, 1994.
Lohrer et al., Carcinogenesis 10 (12): 2279–84, 1989.
Matsubara J. et al., Pharmac. Ther. 39: 331–333, 1988.
Marshall, Science, 269, 1995, 1050–1055.
NIH Report and Recommendations, Dec. 7, 1995, 1–40.
S. Kim et al., "Transcriptional Targeting of Replication–defective Adenovirus Transgene Epxression to Smooth Muscle Cells in Vivo", J. Clin. Invest. vol. 100, No. 5, Sep. 1997, pp. 1006–1014.
Y.J. Kang et al., "Overexpression of Metallothionenin in the Heart of Transgenic Mice Suppresses Doxorubicin Cardiotoxidity", J. Clin. Invest. vol. 100, No. 6, Sep. 1997, pp. 1501–1506.
J. Greenberger, "Prevention of Late Effects of Irradiation Lung Damage by Manganese Superoxide Dismutase Gene Therapy", Gene Therapy: Final Revised, pp. 1–43 (no year).
Xiang, K., "Multiple Taq I RFLPs at the Human Manganese Superoxide Dismutase (SOD2) locus on Chromosome 6", Nucleic Acids Research, vol. 15, No. 18 (1987).
Hyland, V. J. et al., "A 5' Flanking Region of the Metallothionein, MT2A, Gene Identifies Two Moderately Frequent RFLPs", Nucleic Acids Research, vol. 15, No. 3 (1987).
Karin, M. et al., "Human Metallothionein Genes–Primary Structure of the Metallothionein–II Gene and a Related Processed Gene", Nature, vol. 299 (Oct. 28, 1982).

(List continued on next page.)

Primary Examiner—Deborah J. R. Clark
Assistant Examiner—Shin-Lin Chen
(74) Attorney, Agent, or Firm—Foley & Lardner

(57) ABSTRACT

A method of protecting a subject against an agent that elicits production of toxic free radicals, superoxide anions, or heavy metal cations in the subject is disclosed which entails in vivo administration to the subject of a polynucleotide encoding a protein that is transiently expressed in said subject. The transiently expressed protein is capable of neutralizing or eliminating the toxic free radicals, superoxide anions or heavy metal cations that are elicited by the agent. The method is particularly useful in preventing the development of esophagitis during treatment of lung cancer patients with ionizing radiation and/or chemotherapeutic drugs.

23 Claims, 2 Drawing Sheets

OTHER PUBLICATIONS

Sherman, L. et al., "Nucleotide Sequence and Expression of Human Chromosome 21–encoded Superoxide Dismutase mRNA", *Proc. Natl. Acad. Sci. USA*, vol. 80, pp. 5465–5469 (Sep. 1983).

Richards, R. I. et al., "Structural and Functional Analysis of the Human Metallothionein–$I_A$ Gene: Differential Induction by Metal Ions and Glucocorticoids", *Cell*, vol. 37, pp. 263–272 (May 1984).

Lieman–Hurwitz, J. et al., "Human Cytoplasmic Superoxide Dismutase cDNA Clone: A Probe for Studying the Molecular Biology of Down Syndrome", Proc. Natl. Acad. Sci. USA. vol. 79, pp. 2808–2811 (May 1982).

Cai, D. W. et al., "Stable Expression of the Wild–Type p53 Gene in Human Lung Cancer Cells After Retrovirus–Mediated Gene Transfer", Proceedings of the American Association of Cancer Research, vol. 34, pp. 505, 3011 (Mar. 1998).

McCormick, M. L. et al., "Superoxide Dismutase and Catalase Levels During Estrogen–Induced Renal Tumorigenesis, in Renal Tumors and their Autonomous Variants in the Syrian Hamster", *Carcinogenesis*, vol. 12, No. 6, pp. 977–983 (1991).

Englehardt, J. et al., "In Vivo Retroviral Gene Transfer into Human Bronchial Epithelia of Xenografts", The American Society for Clinical Investigation, Inc., vol. 90, pp. 2598–2609 (Dec. 1982).

Oberley, L. W. et al., "Transfection of Manganese Superoxide Dismutase cDNA into Cultured Tumor Cells," *Proc. Amer. Assoc. for Canc. Res.*, Abstract 98 (1993).

Yang, Y. et al., "An Approach for Treating the Hepatobiliary Disease of Cystic Fibrosis by Somatic Gene Transfer", *Proc. Natl. Acad. Sci. USA*, vol. 90, pp. 4601–4605 (May 1993).

Rosenfeld, M. A. et al., "Adenovirus–Mediated Transfer of a Recombinant α1–Antitrypsin Gene to the Lung Epithelium in Vivo", *Reports*, pp. 431–434 (Apr. 19, 1991).

Dunn, M. A. et al., "Minireview—Metallothionein (42525A)", Proceedings of the Society for Experimental Biology and Medicine 185, pp. 107–119 (1987).

Lohrer, H. et al., "Overexpression of Metallothionein in CHO Cells and its Effect on Cell Killing by Ionizing Radiation and Alkylating Agents", *Carcinogenesis*, vol. 10, No. 12, pp. 2279–2284 (1989).

Holland, C. et al., "Enhancer Sequences of a Retroviral Vector Determine Expression of a Gene in Multi–potent Hematopoietic Progenitors and Committed Erythroid Cells", *Proc. Natl. Acad. Sci. USA*, vol. 84, pp. 8662–8666 (Dec. 1987).

Roth, J. et al., "p53 Regulates the Transcription of Human Cytokeratin β Gene in Human Lung Cancer Cell Lines", Proceedings of the American Association for Cancer Research, vol. 34, p. 509 (Mar. 1993).

Petkau, A., "Scientific Basis for the Clinical Use of Superoxide Dismutase", *Cancer Treatment Reviews 13*, pp. 17–44 (1986).

Fujiwara, T. et al., "Retroviral–Mediated Transduction of p53 Gene Regulates TGF–β Gene Expression and Secretion in a Human Glioblastoma Cell Line", Proceedings of the American Association for Cancer Research, vol. 34, pp. 449, 2680 (Mar. 1993).

Georges R. N. et al., "In–Vivo Retroviral Transduction of Antisense K–ras Suppresses Tumor Growth in an Orthotopic Lung Cancer Model", Proceedings of the American Association for Cancer Research, vol. 34, p. 336 (Mar. 1993).

Shiraishi, N. et al., "Elevation in Metallothionein Messenger RNA in Rat Tissues After Exposure to X–Irradiation", *Toxicology and Applied Pharmacology 98*, pp. 501–506 (1989).

Bremner, I. et al., "Metallothionein and the Trace Minerals", *Annu. Rev. Nutr.*, pp. 63–83 (1990).

FLOTTE, T. et al., "Gene Expression from Adeno–Associated Virus Vectors in Airway Epithelial Cells", *Am. J. Respir. Cell Molec. Biol*, 7:349 (1992).

ANKLESARIA, P. et al., "Engraftment of a Clonal Bone Marrow Stromal Cell Line *in vivo* Stimulates Hemato–poietic Recovery from Total Body Irradiation ", *Proc. Natl. Acad. Sci. USA*, vol. 84, pp. 7681–7685,(Nov. 1987).

ARMSTRONG, J. G. et al., "Three Dimensional Conformal Radiation Therapy May Improve the Therapeutic Ratio of High Dose Radiation Therapy for Lung Cancer", *Int. J. Radiation oncology Biol. Phys.*, vol. 00, pp. 001–005 (1993).

GEORGES, R. N. et al., "Prevention of Orthotopic Human Lung Cancer Growth by Intratracheal Instillation of a Retroviral Antisense K–*ras* Construct", *Canver Research 53*, pp. 1743–1746 (Apr. 15, 1993).

STRIBLING, R., "Aerosol Gene Delivery *in vivo*", Proc. Natl Acad Sci. USA, vol. 89, pp. 11277–11281, (Dec. 1992).

FERKOL, T. et al., "regulation of the Phosphoenolpyruvate Carboxykinase/human Factor IX Gene Introduced into the Livers of Adult Rats by Receptor–Mediated Gene Transfer", Methodology, vol. 7, pp. 1081–1091, (Aug. 1993).

ROSENFELD, M. et al., "In Vivo Transfer of the Human Cystic Fibrosis Transmembrane Conductance Regulator Gene", Cell, vol. 68 (Jan. 10, 1992).

MULLIGAN, R., "The Basic Science of Gene Therapy", *Science*, vol. 260, pp. 926–932 (May 14, 1993).

LEDLEY, FD "Clinical Considerations in the Design of Portocols for Soma".

HALLAHAN et al. "Protein Kinase C Mediates X–ray Inducibility of Nuclear Signal Tranducers EGR1 and JUN," *Proc. Natl. Acad. Sci. USA* 88;2156–2160 (Mar. 1991).

DATTA et al., "Ionizing Radiation Activates Transcription of the *EGR1* Gene via CArG Elements," *Proc. Natl. Acad. Sci. USA* 89:10149–10153 (Nov. 1992).

\* cited by examiner

PROTECTION OF THE ESOPHAGUS FROM CHEMOTHERAPEUTIC OR IRRADIATION DAMAGE BY GENE THERAPY

BACKGROUND OF THE INVENTION

The present invention is directed generally to protecting an individual's tissues and cells against the damaging effects of an agent that elicits the production of a free radical, superoxide anion, or heavy metal cation when that individual is exposed to the agent. Specifically, the invention is directed to protection of the oral cavity, oropharynx, esophagus, stomach, small intestine and colon by transient expression of a protective protein through somatic gene transfer in vivo.

Therapeutic concentrations of anti-cancer drugs and clinical radiation therapy are known to damage a patient's normal tissues and cells. A need clearly exists for means to protect a patient's normal tissues during chemotherapy and/or radiation therapy. Previous methods of affording such protection include administration of sulfhydryl compounds such as thiols or other radical scavenger compounds.

The major way in which radiation damages biomolecules and cells is through its interaction with water to produce toxic free radicals (H•, OH•, $e_{aq}^-$) and $H_2O_2$ or, through interaction with oxygen, to produce the superoxide radicals ($ÅO_2^-$). In the late 1940's it was discovered that sulfhydryl compounds, such as cysteine and cysteamine, provide radiation protection in animals. Patt et al., *Science* 110: 213 (1949). Thiol groups scavenge radiation-produced free radicals by donating a hydrogen atom to damaged molecules. Despite extensive efforts to develop more effective protective agents, no thiol-based radioprotector has been found to be significantly better than cysteamine. Mitchell et al., *Arch. Biochem. and Biophys.* 289: 62 (1991). However, the use of thiol drugs to protect against radiation damage is limited by the toxicity of such compounds.

Antineoplastic agents, particularly the class of chemotherapeutic drugs known as alkylating agents, also produce free radicals that are cytotoxic due to their ability to form covalent bonds with nucleic acids. Most alkylating agents form positively charged carbonium ions that yield the charged alkylating intermediate $R-CH_2-CH_2^+$ which attacks electron-rich sites on nucleic acids, proteins, small molecules and amino acids.

Several endogenous intracellular scavengers of free radicals, superoxide radicals and heavy metal cations have been identified. Induction or elevated activities of each of metallothionein (MT), gamma-glutamyl transpeptidase (γ-GTP) and superoxide dismutase (SOD) are known to provide resistance to ionizing radiation damage in vitro. These proteins function intracellularly to scavenge free radicals, superoxide anions or heavy metal cations. U.S. Pat. No. 5,599,712, the contents of which are incorporated by reference in their entirety, describes a method for providing functional intracellular therapeutic levels of metallothionein, superoxide dismutase or gamma glutamyl transpeptidase to protect normal lung tissue from the adverse effects of a combination of chemotherapy and radiation therapy.

SUMMARY OF THE INVENTION

It is therefore an object of the present invention to provide a method of protecting normal cells not at a tumor site against the damaging effects of an anticancer agent or ionizing radiation by providing genes encoding protein protective to normal somatic cells.

It is a further object of the present invention to provide a method of protecting normal cells, particularly cells of the oral cavity, oropharynx, esophagus, stomach, small intestine and colon, against the damaging effects of an anticancer agent or ionizing radiation by providing genes encoding protein protective to normal somatic cells.

It is another object of this invention to provide a safe and efficient method of transferring oxidation or cation-scavenging protein encoding genes directly into cells of the oral cavity, oropharynx, esophagus, stomach, small intestine and colon.

It is yet another object of this invention to transfer oxidation or cation-scavenging protein encoding genes directly into cells of the oral cavity, oropharynx, esophagus, stomach, small intestine and colon using an easily administrable method.

Another object of the present invention is to provide transient expression of the oxidation or cation-scavenging protein in the cells of the oral cavity, oropharynx, esophagus, stomach, small intestine and colon to protect these cells against an anticancer agent, wherein either the transferred polynucleotide or gene is cleared after therapeutic courses of ionizing radiation therapy or chemotherapy, or the transferred polynucleotide or gene is stably integrated within the genome, but its expression is temporary, and induced for a limited time by the ionizing radiation therapy or chemotherapy.

In accomplishing these and other objects, there has been provided, in accordance with one aspect of the present invention, a method for protecting the oral cavity, oropharynx, esophagus, stomach, small intestine or colon in a subject against an agent that elicits production of a toxic species when the subject is exposed to the agent. Alternatively, the present invention provides a method for protecting tissues of a subject against an agent that elicits production of a toxic species when the subject is exposed to the agent, wherein the tissues to be protected are at a site remote from the tissues to be treated with toxic species. The toxic species is selected from the group consisting of a free radical, a superoxide anion, and a heavy metal cation. Each of the methods comprises administering to the subject in vivo a pharmaceutical composition comprising (A) a polynucleotide that encodes a protein that is transiently expressed in the subject, wherein the protein is capable of neutralizing or eliminating the toxic species, and (B) a pharmaceutically acceptable vehicle for the polynucleotide. The agent may be ionizing radiation, clinical radiation therapy, or a chemotherapeutic drug. In a preferred embodiment of the invention, the proteins of the invention which neutralize or eliminate the toxic species are gamma glutamyl transpeptidase, manganese superoxide dismutase, or metallothionein. In one embodiment of the invention, the pharmaceutical composition of the invention comprises a mixture of polynucleotides selected from a polynucleotide encoding gamma glutamyl transpeptidase, a polynucleotide encoding manganese superoxide dismutase or a polynucleotide encoding metallothionein.

Liposomes, an adenovirus vector, or ligand-DNA conjugates can be used to introduce a polynucleotide according to the invention. Administration of the pharmaceutical composition preferably is performed prior to a subject's exposure to an agent. The present method is used during treatment of a variety of cancers, including lung cancer, prostate cancer, cervical cancer, endometrial cancer, ovarian cancer and bladder cancer.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A illustrates the Wild-type Adenovirus type 5 (Ad5) genome showing the E1a, E1b and E3 regions and the portion to be deleted from the left end of Ad5 for insertion of the appropriate expression cassettes. An expression cassette is a nucleic acid construct that includes, as operably linked components in the direction of transcription, a transcriptional initiation region, a nucleic acid sequence encoding a protein of interest and a transcriptional termination region wherein the transcriptional regulatory regions are functional in the targeted mammalian host cell. FIG. 1B illustrates an expression cassette containing regulatory sequences and a recombinant DNA sequence encoding metallothionein.

FIG. 2A illustrates the Wild-type adenovirus type 5 (Ad5) genome showing the E1a, E1b and E3 regions and the portion to be deleted from the left end of Ad5 for insertion of the appropriate expression cassettes. FIG. 2B illustrates an expression cassette containing regulatory sequences and a recombinant DNA sequence encoding γ-GTP.

FIG. 3A illustrates the Wild-type adenovirus type 5 (Ad5) genome showing the E1a, E1b and E3 regions and the portion to be deleted from the left end of Ad5 for insertion of the appropriate expression cassettes. FIG. 3B illustrates an expression cassette containing regulatory sequences and a recombinant DNA sequence encoding manganous superoxide dismutase.

DETAILED DESCRIPTION OF THE INVENTION

Figure 1A:
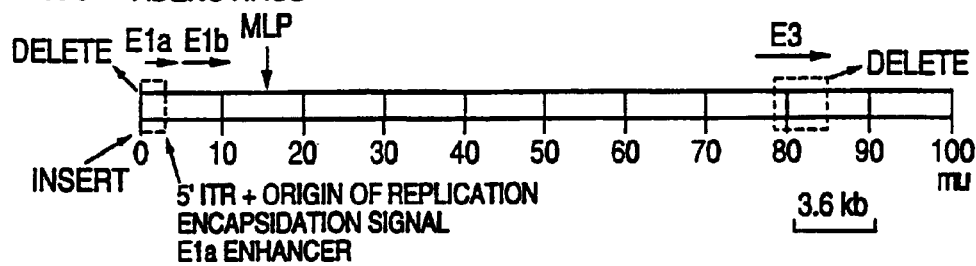
FIGS. 1A and 1B are schematic drawings of the construction of a Metallothionein (MT) recombinant adenovirus vector (Ad-MT) of the present invention.

Ionizing radiation produces toxic free-radical species. Antineoplastic agents, particularly the class of chemotherapeutic drugs known as alkylating agents, also produce free radicals that are cytotoxic because of their ability to form covalent bonds with nucleic acids. Most alkylating agents, including cyclophosphamide, nitrogen mustard, melphalan, chlorambucil, busulfan, nitrosourea, cis-platinum, streptozotocin, aziridinylbenzoquinone (AZQ), dicarbazine (DTIC), mAMSA and mitoxantrone, form positively charged carbonium ions that yield a charged alkylating intermediate R—$CH_2$—$CH_2^+$ that attacks electron-rich sites on nucleic acids, proteins, small molecules and amino acids. Chabner et al., in CANCER; PRINCIPLES AND PRACTICE OF ONCOLOGY, 2nd edition, DeVita et al. (eds.) (J. B. Lippincott Co., Philadelphia 1985).

The method of the present invention provides a means for protecting normal cells, particularly cells of the oral cavity, oropharynx, esophagus, stomach, small intestine and colon, of an individual against an agent that elicits the production of a free radical, a superoxide anion, and/or a heavy metal cation. The cells to be protected may be a site remote from the tumor site. The method of the present invention employs gene therapy, which is the transfer of genetic material into specific cells of a patient.

Transient gene expression, according to the present invention, can result by one of two mechanisms. Gene transfer can be used to introduce DNA sequences into the nucleus in an unintegrated form. In that case, transient expression, or nonintegrated expression is limited by the stability of the nonintegrated DNA molecule(s) and may persist for extended periods of time, but rarely persists for periods longer than about one to three weeks. Alternatively, a gene or polynucleotide may be stably integrated into the genome. A gene that is transferred to an individual is called a transgene.

The gene therapy method of the present invention involves an in vivo method of gene therapy that provides a polynucleotide encoding a protein capable of neutralizing or eliminating a toxic free radical, superoxide anion and/or heavy metal cation, wherein the protein is transiently expressed in the individual. The transgenes of the present invention encode protein(s), such as metallothionein, superoxide dismutase or gamma glutamyl transpeptidase, that scavenge a toxic free radical, superoxide anion and/or heavy metal cation.

γ-Glutamyltranspeptidase (γ-GTP) is a plasma membrane-associated ectoenzyme that catalyzes the transpeptidation of extracellular glutathione into amino acid intermediates, which are then transported across the cell membrane and used to resynthesize glutathione de novo. Glutathione (GSH) detoxifies free-radicals. Cells generally synthesize GSH de novo from the constituent amino acids. A cell's sensitivity to radiation is directly correlated with its ability to transpeptidate extracellular glutathione via γ-GTP. Cell lines with high γ-GTP activity are more resistant to the effects of radiation and are more capable of repairing damage induced by low doses of γ-irradiation than cell lines with low γ-GTP activity. See Examples 7 and 8. Tumor cells depleted of GSH have been shown to be more susceptible to ionizing irradiation and chemotherapeutic agents because GSH-dependent detoxification pathways are reduced. Louie et al., *Cancer Res.* 45: 2110 (1985).

Protection against superoxide radicals requires antioxidants, such as GSH, and the $O_2^-$-scavenging enzyme superoxide dismutase (SOD). SODs are metalloenzymes that are essential for dismutation of $O_2^-$ to $H_2O_2$ and $O_2$. There are three forms of SODs: copper-zinc (CuZnSOD), manganous (MnSOD) and iron (FeSOD). Although CuZn-SOD and FeSOD are made constituitively, MnSOD synthesis is inducible. Induction of MnSOD activity has been shown to follow X-irradiation of heart tissue. Oberley et al., *Arch. Biochem. Biophys.* 254: 69 (1987). Further, hematopoietic tumor cell lines transfected with MnSOD cDNA in vitro demonstrate increased resistance to radiation. Suresh et al., *Experimental Hematology* 21: 1828 (1993).

Metallothioneins are low molecular weight proteins consisting of a single polypeptide chain of 61 amino acid residues, of which 20 are cysteines that chelate cations. Induction of metallothionein has been shown to provide resistance to ionizing irradiation damage. Metallothionein protein protects cells from the toxic effects of heavy metal ions and is a powerful scavenger of radiation-induced OH-radicals in vitro. Cells lines that express high levels of MT are resistant to DNA damaging agents, such as cis-platinum and chlorambucil, and ionizing radiation. Andrews et al., *Cancer Chemother. Pharmacol.* 19:149 (1987); Bakka et al., *Experientia* 38:381 (1982); Matsubara et al., *Environ.*

Res. 43:66 (1987). Metallothionein is capable of scavenging free radicals produced by electrophilic anticancer drugs and ionizing radiation in vitro. Endresen et al., *Cancer Res.* 43:2918 (1983); Thornalley et al., *Biochim., Biophys. Acta* 827:36 (1985). Importantly, induction of MT in mouse liver provides protection against lethal damage from high dose radiation. Matsubara et al., *Rad. Res.* 111:267 (1987). Nonetheless, some cell lines transfected with the MT gene in vitro were as sensitive to ionizing radiation and bleomycin as non-transfected recipient cells. However, MT transfected cells were resistant to mitomycin, suggesting that MT protein protects some cells in vitro from monofunctional alkylating and cross-linking agents but not from free radicals. Lohrer et al., *Carcinogenesis* 10:2279 (1989).

A DNA sequence encoding an entire superoxide dismutase, preferably MnSOD, coding region can be isolated or synthesized by methods well known to the art based on the MnSOD sequences reported by Oursler et al., *J. Cell. Biochem.* 46:219 (1991) or Beck et al., *Nucl. Acids. Res.* 15:9076 (1987), or the SOD sequences reported by U.S. Pat. No. 4,751,180; Lieman-Hurwitz et al., *Proc. Natl. Acad. Sci. USA* 79: 2808 (1982); U.S. Pat. No. 4,742,004; Xiang et al., *Nucleic Acids Res.* 15: 7654 (1987) or Sherman et al., *Proc. Natl. Acad. Sci. USA* 80: 5465 (1983), the contents of each of which are incorporated by reference in their entirety. Alternatively, these sequences can be prepared by the polymerase chain reaction by methods well known to those of skill in the art. See, e.g., Wong et al., *Cell* 58:923 (1989).

DNA sequences encoding various species and isoforms of metallothionein can be isolated or synthesized by methods well known to the art based on the sequences reported for human MT by [Yamazaki et al., *Biochem Int.* 28:451 (1992); Soumillion et al., *Eur. J. Biochem.* 209: 999 (1992); Karin et al., *Proc. Natl. Acad. Sci. USA* 80: 4040 (1983); Paliwal et al., *Neurochem. Int.* 17: 441 (1990); Schmidt et al., *J. Biol. Chem* 260: 7731 (1985); Richards et al., *Cell* 37: 263 (1984); Karin et al., *Nature* 299: 797 (1982); Hyland et al., *Nucleic Acids Res.* 15: 1350 (1987);, sheep and mouse [Peterson et al., *Eur. J. Biochem.* 160: 579 (1986)], fish [(Lee et al., *Korean Biochem J.* 25: 48 (1992); Bonham et al., *DNA* 6: 519 (1987)] and insect [Lastowski-Perry et al., *J. Biol. Chem.* 260: 1527 (1985)], the contents of each of which are incorporated by reference in their entirety. Preferably, the human metallothionein sequences disclosed by either Yamazaki et al., (1992) supra, or Soumillion et al., (1992) supra are used in the method of the present invention.

DNA encoding γ-GTP can be provided for use in the present invention by isolating or synthesizing such a sequence by methods well known to the art based on the sequences reported by any of Altman et al., *Biochemistry* 32: 3822 (1993); Ishiye et al., *Biotech. Progr.* 9: 323 (1993); Ishiye et al, *FEMS Mirobiol. Lett.* 97: 235 (1992); or Angele et al., *Clin. Chem.* 37: 662 (1991), the contents of each of which are hereby incorporated by reference. DNA encoding MT, SOD, MnSOD, or γ-GTP can be provided for use in the present invention by methods well known to those of skill in the art, such as (1) oligonucleotide synthesis of the desired DNA sequences based on the sequences disclosed in the above recited references; (2) isolation of the desired DNA sequences from the plasmids disclosed in the above references or from plasmids available from American Type Culture Collection (ATCC) (12301 Parklawn Drive, Rockville, Md. 20852) such as: [a] ATCC 57117—pHM6 containing the human metallothionein 2 pseudogene 1; [b] ATCC 57152, 57153 —bMT-IIA containing the human metallothionein 2 gene; [c] ATCC 20745—pYAS11 containing cDNA encoding human superoxide dismutase 1; [d] ATCC 20796—pYLUIGF2-14 containing DNA encoding human superoxide dismutase 1; [e] ATCC 39786—pSOD alpha 2 containing DNA encoding human superoxide dismutase 1; [f] ATCC 59946, 59947—phMnSOD4 containing DNA encoding human superoxide dismutase 2; [g] ATCC 61646, 61647 containing cDNA encoding human superoxide dismutase 1; [h] ATCC 86406—IB881 containing cDNA encoding human superoxide dismutase or (3) polymerase chain reaction amplification of the desired DNA sequences from the DNA libraries disclosed in the above references using primers based on the sequences disclosed in the recited references.

Transient expression of genes administered in vivo is viewed in this art as a major technical limitation to gene therapy. See Mulligan, *Science* 260: 926 (1993). In sharp contrast, according to the present invention transient expression of the genes is highly desirable because protection of the normal tissue is needed only for the period of radiation therapy or chemotherapy; thereafter, rapid clearance of the gene product is desirable. Transient expression is desirable because the prolonged clinical effects of elevated MT, γ-GTP and/or MnSOD are unknown. Also, clearing of the transgene and its vector may be clinically desirable after chemotherapy or radiation therapy to provide for the next phase of a combined modality therapeutic approach. The methods of the present invention are designed to result in transient or nonintegrated expression of an exogenous gene in vivo; however, in the event that a limited amount of stable integration of the exogenously provided DNA also results, the method of the present invention remains functional in its ability to provide a protein capable of neutralizing or eliminating a toxic ionic species in vivo.

Transient expression can be achieved by directed introduction of the genetic material encoding the desired proteins into cells or by use of a heterologous virus genome as a vector. Methods for delivering genes into mammalian cells to provide transient expression that can be utilized for gene therapy include: papovaviruses, adenovirus, vaccinia virus, herpesviruses, poxviruses, polio virus, sindbis and other RNA viruses, ligand-DNA conjugates, adenovirus-ligand-DNA conjugates, naked DNA, lipofection and receptor-mediated gene transfer. See, eg., Mulligan, supra. Coen in VIROLOGY, Fields et al. (eds.) Raven Press, Ltd., (New York, 1990); Ferkol et al., *FASEB* 7: 1081 (1993). Animal model studies have efficiently transferred genes using retroviruses (Friedmann, *Science* 244: 1275 (1989)), adenoviruses (Rosenfeld et al., *Science* 252: 431 (1991); Rosenfeld et al., *Cell* 68: 143 (1992)) and liposomes (Felgner et al., *Nature* 349: 351 (1991).

Transient expression is achieved by virtue of an inducible transcriptional promoter to control the expression of the gene or polynucleotide. In a preferred embodiment, the inducible promoter is induced directly or indirectly by the ionizing radiation therapy or chemotherapy agent itself. A suitable promoter is the erg1 promoter, a promoter induced by irradiation. Hallahan et al., *Proc. Natl. Acad. Sci. USA* 88: 2156–2160 (1991) and Datta et al., *Proc. Natl. Acad. Sci. USA* 89: 10149–10153 (1992). Transcription of polynucleotide(s) or gene(s) controlled by erg-1 stops somewhere between 60 and 90 hours post induction.

The method of the present invention can be used to protect specific tissues in cancer patients against the damaging effects of ionizing radiation and chemotherapeutic drugs, which produce free radicals, superoxide anions, and/or heavy metal cations. In particular, the method of the present invention can be used to transfer a gene to normal cells at a site remote from the tumor site prior to clinical radiation therapy or chemotherapeutic drug administration to combat cancer. In particular, the method of the present invention can be used to transfer a gene to normal cells of the oral cavity, oropharynx, esophagus, stomach, small intestine or colon prior to clinical radiation therapy or chemotherapeutic drug administration to combat lung, prostate, bladder, cervical or endometrial cancer, for example.

In one preferred embodiment, the method of the present invention is directed toward transient in vivo gene therapy to lung cancer patients to provide protection of the oral, cavity, oropharynx and esophagus when the lung cancer is treated with ionizing radiation therapy or anti-neoplastic alkylating agents. A limiting factor in the treatment of lung cancer, particularly with treatments regimens that entail a combination of radiation therapy and chemotherapy with paclitaxel, vinblastine, or cis-platinum, has been the development of esophagitis during the radiation treatments. In some cases, patients cannot complete a course of therapy because of the development of severe esophagitis. The esophagitis is the result of injury to the mucosa layer of the esophagus. After irradiation, there is an increase in the mitotic activity in the mucosa to repair the damage. Paclitaxel, in particular, works by blocking mitosis during $G_2/M$, the portion of the cell cycle which is the most radiosensitive. It is hypothesized that the combination of the inhibition of mitosis by the chemotherapeutic agent and the sensitization of the mucosal cells during irradiation prevents repair of mucosal damage and causes the esophagitis.

In another embodiment, the method of the present invention is directed toward transient in vivo gene therapy to prostate, bladder, cervical or endometrial cancer patients to provide protection to the small intestine and colon when these cancers are treated with ionizing radiation therapy or anti-neoplastic alkylating agents. The mechanism is the same as that described above for esophageal protection. In this case, it is hypothesized that the combination of inhibition of mitosis by the chemotherapeutic agent and the sensitization of the mucosal cells during irradiation prevents repair of mucosal damage to intestinal crypt cells and colon crypt cells.

In addition to protection of normal cells at a site remote from the tumor site prior to clinical radiation therapy or chemotherapeutic drug therapy, the method of the present invention also is useful to protect normal cells of the oral cavity, oropharynx, esophagus, stomach, small intestine and colon during treatment of a tumor in the same region. In this case, the transgene is delivered and expressed more efficiently in normal tissue as compared to tumors of such tissue. More efficient expression in normal tissue than in tumor tissue has been confirmed by studies in experimental animals, e.g., rats or mice. A lower expression of the transgene in tumor cells transplanted into the animals as compared to the normal surrounding tissue confirms a lower ratio of delivery of therapeutic genes to tumor cells than normal cells targeted for protection.

Compositions for use in the present method comprise a polynucleotide that encodes a protein that is transiently expressed in a subject when the subject is exposed to an agent that elicits production of a toxic species, such as a free radical, a superoxide anion, or a heavy metal cation, wherein the protein is capable of neutralizing or eliminating the toxic species; and a pharmaceutically acceptable vehicle for the polynucleotide. In this context a pharmaceutically acceptable vehicle is inert or otherwise medically acceptable, and is compatible with the active agent, in a particular context of administration. In addition to a suitable excipient, a pharmaceutically acceptable carrier can contain conventional additives like diluents, adjuvants, antioxidants, dispersing agents and emulsifiers, anti-foaming agents, flavor correctants, preservatives, solubilizing agents and colorants. More particularly, pharmaceutically acceptable vehicles are characterized by having physiologically acceptable pH and ionic strength. Sterile, buffered saline, particularly phosphate-buffered saline, is a preferred vehicle for compositions to be administered parenterally.

A preferred embodiment uses artificial lipid membranes (i.e., liposomes) for delivery. Procedures for introducing DNA into cells that employ lipid include: polyethylene glycol to mediate fusion of protoplast derived from plasmid-containing bacteria (Schaffner, *Proc. Natl. Acad. Sci. USA* 77: 2163 (1980); DNA-containing erythrocyte ghosts (Wiberg et al., *Nucleic Acids Res.* 11: 7287 (1983); DNA-containing liposomes (Fraley et al., *Proc. Natl. Acad. Sci. USA* 76: 3348 (1979); plasmid/cationic liposome complexes (Stribling et al., *Proc. Natl., Acad. Sci. USA* 89: 11277 (1992); WO93/12756) and lipofection (Felgner et al., *Proc. Natl. Acad Sci. USA* 84: 7413 (1987). The gene therapy method of the present invention can employ any of the above procedures for introducing genetic material into cells in vivo, but lipofection with plasmid/cationic liposome complexes is a preferred method.

Lipofection employs a liposome formulation of cationic lipid to transfect nucleic acids into cells. The lipid-nucleic acid complex fuses with plasma membranes and transfers the nucleic acid into the cells efficiently, where the DNA is expressed. Lipofection is five to one hundred times more efficient in introducing DNA into cells than calcium phosphate or DEAE-dextran transfection methods. Chang et al., *Focus* 10: 66 (1988). Liposome preparations can be prepared as described in the art or purchased from commercially-available sources, such as GIBCO BRL's lipofectin (GIBCO BRL, Life Technologies, Inc., P.O. Box 9418, Gaithersburg, Md. 20898). Felgner et al., (1987) supra; Schreier, *J. of Liposome Res.* 2: 145 (1992); Chang et al., (1988) supra.

Transient transfection employing lipofection is measured 24 to 72 hours after transfection by assays that measure gene expression of the transfected gene(s). Commonly used assays monitor enzyme activities of chloramphenicol acetyl-transferase (CAT), LAC-Z, β-galactosidase, luciferase, or human growth hormone that can be contained in the constructs. Using lipofection, human small cell lung cancer cells have been transiently transfected. Chang et al. supra. Lipofection of DNA encoding MT, CuZnSOD, FeSOD, MnSOD and -GTP encoding DNA to any target tissue can be performed using lipofection techniques well known to those of skill in the art.

A preferred preparation of a cationic lipid preparation is composed of 1:1 DOTMA or DDAB/DOPE (i.e., 1:1 of N-[1-(2,3-dioleyloxy)propyl]-N,N,N-triethylammonium (DOTMA) or dimethyldioctadecyl-ammoniumbromide (DDAB) and cholesterol and dioleoyl phosphatidylethanolamine (DOPE). To produce 1:1 DOTMA/DOPE cationic liposomes, stock solutions of lipids are dissolved in chloroform and stored under argon at −20° C. Lipids are mixed in round bottomed flasks and evaporated to dryness on a rotary evaporator under reduced pressure. Final lipid concentrations of 10 mM each are made by adding double-distilled water. The resulting mixture is sonicated to produce a suspension of liposomes.

Plasmid is complexed to DOTMA/DOPE liposomes as follows. Plasmid DNA and DOTMA/DOPE liposomes are diluted separately in water prior to being mixed. The volume of water may range between 1 and 20 ml, preferably about 8 ml. The composition of the liposome-DNA complex may range from about 4:1 to about 1:10 micrograms DNA to nanomoles of cationic lipid, preferably from about 1:1 to 1:2 micrograms DNA to nanomoles of cationic lipid.

Alternatively, to specifically transfer DNA capable of expressing γ-GTP, MT, SOD and/or MnSOD in a desired/particular human target tissue in vi vo, replication-deficient recombinant adenoviruses can be used. For example, Ad.CMV-lacZ (containing cytomegalovirus) and Ad.CB-MnSOD viruses, which are based on adenovirus type 5 (Ad5) and produced by homologous recombination in transformed primary human embryonal kidney cell line 293 (ATCC Catalogue Number CRL1573), can be used in the method of the present invention. Graham et al., METHODS IN MOLECULAR BIOLOGY (Murray, Humana, 1991).

To construct a recombinant adenovirus according to the present invention, approaches well known to those of ordinary skill in the art can be utilized. For example, a recombinant adenovirus of the present invention can be constructed from an adenovirus type 5 (Ad 5) deletion mutant, such as Ad-dl324 (Thimmappaya et al., *Cell* 31: 543 (1982)) and a plasmid containing the Ad5 5' inverted terminal repeat, origin of replication, encapsidation signal, E1a enhancer, the major late promoter, the tripartite leader sequence cDNA and the DNA sequence encoding the entire protein sequence of human MT, γGTP or MnSOD and the SV40 early polyadenylation signal. The recombinant vectors Ad-MT, Ad-γ-GTP, and Ad-MnSOD are constructed by deleting the majority of the E3 region and 2.6 mu from the left end of Ad5 and adding to the left end the MT, γ-GTP or MnSOD expression cassettes, which contain the regulatory sequences and the recombinant MT, γ-GTP or MnSOD encoding DNA. The left end of the viral genome, including the E1a and the majority of the E1b region is deleted and replaced by the MT or γGTP or MnSOD expression cassette containing the essential viral cis-acting elements, including the inverted terminal repeat, an origin of replication, the encapsidation signal, the E1a enhancer and no E1a structural gene. Preferably, the E1a enhancer is followed by the adenovirus type 2 major late promoter and cDNA encoding the MT, γGTP or MnSOD. The constructed recombinant adenovirus is then replicated in a permissive cell line that contains a functional E1a gene to provide a trans-acting E1a protein, such as the 293 human kidney cell line. Thereafter, high titer, infectious recombinant adenoviral stocks are prepared.

Another way to produce a recombinant adenoviral vector is to coprecipitate a linearized plasmid containing the desired cDNA encoding MT, γ-GTP or MnSOD with the large fragment of compatibly cut Ad-dl324 DNA using the calcium-phosphate precipitation method. Graham et al., *Virology* 52: 456 (1973); Wigler et al., *Cell* 14: 725 (1978). The co-precipitated DNAs are then cotransfected into 293 cells to allow homologous recombination to occur. Recombinant adenovirus DNA is tranfected into 293 cells (Graham et al., *J. Gen. Virol.* 35: 59 (1977); Graham et al., *Virology* (1973), supra) where it is replicated, encapsidated into an infectious virus and isolated by plaque purification. Individual plaques are amplified by propagation in 293 cells and viral DNA is extracted. Hirt, *J. Mol. Diol.* 26: 365 (1967).

Recombinant adenovirus plaques containing the human gamma glutamyl transpeptidase, manganese superoxide dismutase and metallothionein protein cDNA (Ad-γGTP; Ad-MnSOD, and Ad-MT respectively) then are identified by restriction cleavage, Southern analysis and/or Northern analysis using the appropriate DNA probes. Control virus having a deletion of the E1a region and not containing the DNA of interest will not demonstrate detectable γ-GTP, MnSOD or MT transcripts in a Northern analysis whereas constructs containing the DNA of interest will demonstrate a detectable γ-GTP, MnSOD or MT transcript.

Each of Ad-γ-GTP, Ad-MnSOD, and Ad-MT vectors are propagated in 293 cells and recovered 36 hours after infection by several cycles of freeze/thawing. All viral preparations are purified by $CaCl_2$ density centrifugation, dialyzed and stored in virus dialysis buffer (10 mM Tris-HCl, pH 7.4, 1 mM $MgCl_2$) at 4° C. for immediate use, or frozen at −70° C. with the addition of 10% glycerol. The titer of the viral stock is determined by plaque assays using 293 cells. Any tissue of the human body can be targeted for the gene therapy of the present invention using the adenoviral vectors described above.

For evaluation of MT, γ-GTP or MnSOD mRNA, or protein synthesis or the evaluation of functional protein, the recombinant vector is used to infect either 293 cells or rat respiratory epithelial cells. To obtain rat respiratory epithelial cells, rats are sacrificed, the lungs and trachea are isolated. Cells are obtained by cytologic brush (Rosenfeld et al., supra (1991) plated, and infected with $2\times10^7$ plaque forming units (PFU) of Ad-MT, Ad-γ-GTP, or Ad-MnSOD in media, or, as a control, exposed to only media.

According to the present invention, conditions are established for achieving recombinant gene expression in a majority of the cells of the target organ to be protected in vivo. It may not be necessary to achieve greater than 50% transgene expression or even greater than 10% transgene expression if cell-to-cell protection is involved in the transfected organ. For example, one transgene expressing cell may be able to protect ten non-transfected cells in a local niche by cell-to-cell transfer of intermediates (e.g., one nucleotide or one nucleoside) involved in the cellular repair cascade.

Dosages of the pharmaceutical compositions administered according to this invention are generally known in the art. The dosage of liposome-DNA complex may range from about 5–50 mg plasmid per 5 to 100 μmoles of liposomes, preferably about 12 mg plasmid per 24 μmoles liposome. Preparations using adenovirus according to the invention are dispensed in dosage unit form comprising between $10^6$ and $10^{14}$ PFU/ml of viral vector in a pharmaceutically acceptable carrier per unit dosage, preferably about $10^{10}$ to $5\times10^{13}$ PFU/ml of the replication-deficient adenovirus Ad-γ-GTP, Ad-MnSOD and/or Ad-MT. The desired pfu are contained in a total volume of between 0.3 and 2.0 ml of phosphate buffered saline (PBS) and administered by techniques known to one skilled in the art. When a ligand-DNA complex is utilized to deliver the desired gene to the target cells, the ligand conjugate is complexed to plasmid DNA using a molar ratio of carrier to DNA of between approximately 10:1 and 500:1, preferably between 300:1 and 500:1.

For protection of the oral cavity, oropharynx, esophagus, stomach and small intestine, compositions for use in the method preferably are administered orally. For example, protection of the oral cavity, oropharynx and esophagus, is achieved by having patients swallow plasmid liposome complex daily before radiotherapy. Typical therapy to tumors in the chest comprises 30–35 radiation treatments over 6½–7½ weeks. For lung cancer, patients typically receive between 6000 and 7000 cGy of irradiation to the lung cancer tumor volume. For protection of the stomach and small intestine, slow-release formulations that are encapsulated with an enteric coating are used. The enteric coating is designed to release the active complex in the organ to be protected. For protection of the colon, the composition preferably is administered by enema or by fiber-optic colonoscope entry into the colon up to the cecum. Generally this treatment is not given daily, but every other day or three times a week, especially in the case of administration by fiber-optic colonoscope.

The following examples illustrate specific embodiments according to the present invention, but do not limit the scope of the invention in any way. Further aspects and variations of the invention, based on the disclosure above and the following examples, will be apparent to the person of ordinary skill in the art.

EXAMPLE 1

Construction of recombinant adenoviral vectors Ad-MT,Ad-MnSOD and Ad-γ-GTP

Figure 1B:
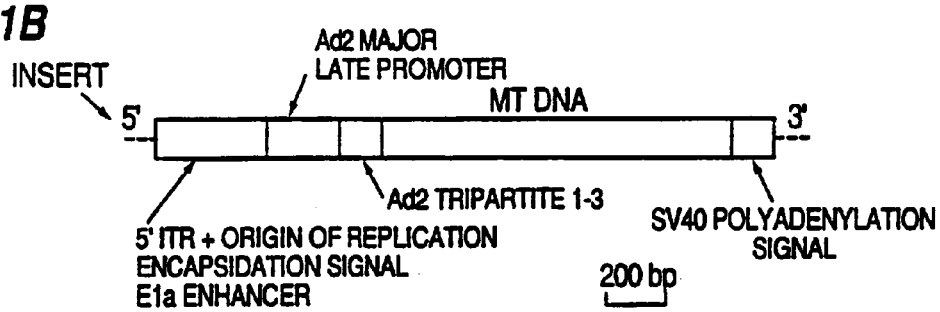

The adenovirus major late promoter is linked to a recombinant human MT gene (Yamazaki et al., supra; Soumillion et al., supra) and is incorporated into a replication-deficient recombinant. Straus in THE ADENOVIRUSES, Ginsberg (ed.) (Plenum Press, New York 1984); Gilardi et al., *FEBS Lett.* 267: 60 (1990). The vector has a deletion of part of the E3 region and part of the viral E1a coding sequence, yet contains an insert of an MT expression cassette (FIGS. 1A and 1B). Ad-MT is constructed by deleting the majority of the E3 region and a portion of the left end of Ad5 and adding to the left end of the MT expression cassette from a plasmid containing the nucleic acid sequence encoding MT.

Figure 2A:
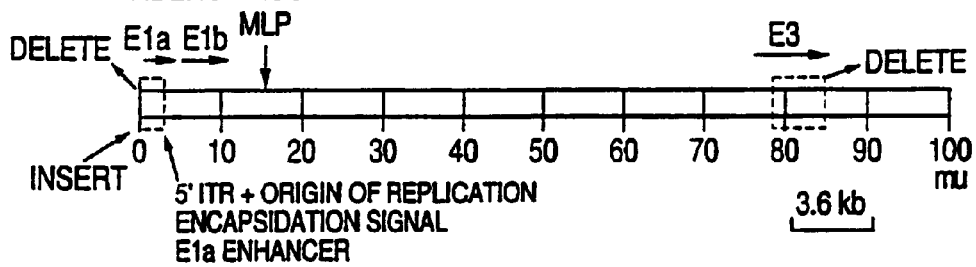
FIGS. 2A and 2B are schematic drawings of the construction of a gamma-glutamyltranspeptidase recombinant adenovirus vector (Ad-γ-GTP).
Figure 2B:
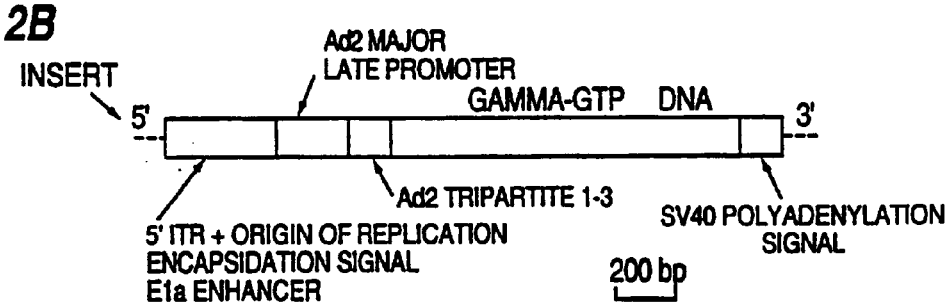

The adenovirus major late promoter is linked to a recombinant human γ-GTP gene (Altman et al., *Biochemistry* 32: 3822 (1993) and incorporated into a replication-deficient recombinant. Straus, supra; Gilardi et al., supra. The vector has a deletion of part of the E3 region and part of the viral E1a coding sequence, yet contains an insert of an γ-GTP expression cassette (FIGS. 2A and 2B). Ad-γ-GTP is constructed by deleting the majority of the E3 region and a portion of the left end of Ads and adding the left end of the γ-GTP expression cassette from a plasmid containing the nucleic acid sequence encoding γ-GTP.

Figure 3A:
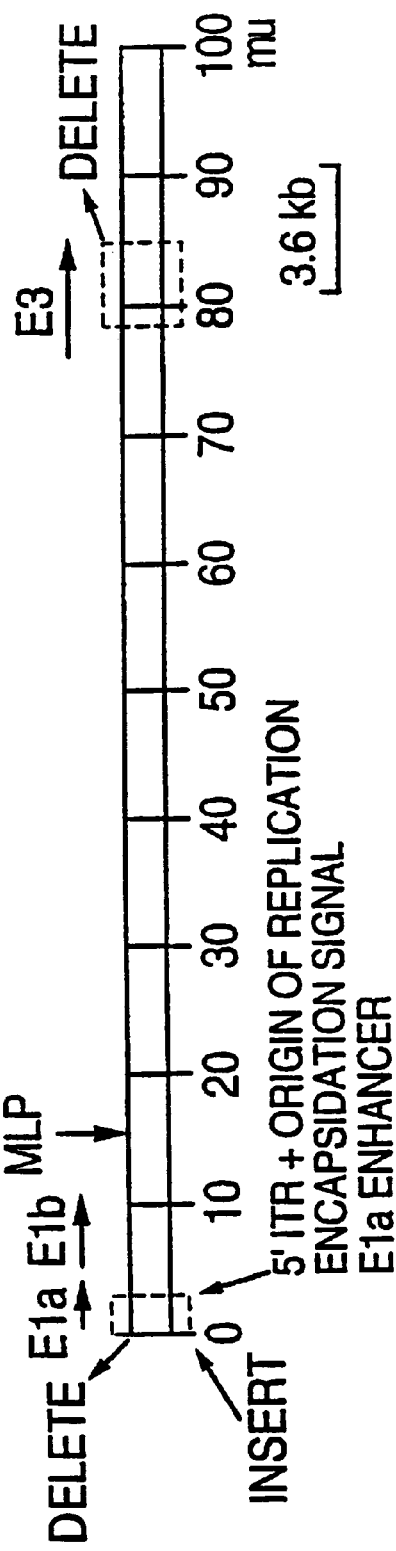
FIGS. 3A and 3B are schematic drawings of the construction of a manganese superoxide dismutase recombinant adenovirus vector (Ad-MnSOD).
Figure 3B:
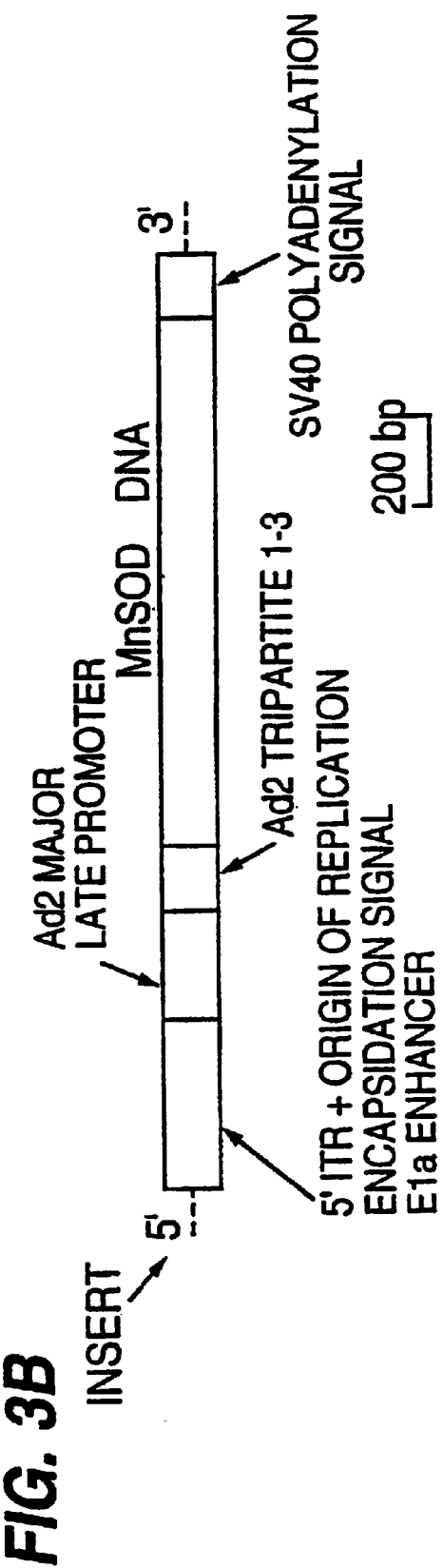

The adenovirus major late promoter is linked to a recombinant human MnSOD gene (Beck et al., *Nucl. Acids. Res.* 15: 9076 (1987)) and is incorporated into a replication-deficient recombinant. Straus, supra; Gilardi et al., supra. The vector has a deletion of part of the E3 region and part of the viral E1a coding sequence, yet contains an insert of an MnSOD expression cassette. Ad-MnSOD is constructed by deleting the majority of the E3 region and a portion of the left end of Ad5 and adding to the left end of the MnSOD expression cassette from a plasmid containing a nucleic acid sequence encoding MnSOD (FIGS. 3A and 3B)

In each case, once the expression cassette is packaged into an infectious, replication-deficient virus, recombinant vector is capable of directing the synthesis of human MT, human γ-GTP, human MnSOD, respectively, in vitro in 293, CHO and HeLa cell lines. Gilardi et al., supra. Expression is confirmed by functional assays.

EXAMPLE 2

In vivo expression of MT, γ-GTP and MnSOD following transfection with recombinant adenoviral vectors Ad-MT, Ad-γ-GTP, and/or Ad-MnSOD Ad-MT, Ad-γ-GTP, or Ad-MnSOD, or a combination of (a) Ad-γ-GTP and Ad-MT, or (b) Ad-γ-GTP and Ad-MnSOD, or (c) Ad-MT and Ad-MnSOD or (d) each of Ad-MT and Ad-MnSOD and Ad-γ-GTP, is used to transfect esophageal tissue of C3H/HeNsd mice in vivo. The mice are injected by passing a tube attached to a 28 gage needle through the oral cavity and depositing recombinant vector at the top of the esophagus. A solution of naked-DNA, at the same concentration as that used in the active preparation, serves as a control.

The mice are sacrificed 24 hours later, and the esophagus removed. The tissue is tested for: (1) immunoreactive MT, MnSOD, or γ-GTP, as measured by immunoprecipitation or Western blotting, and (2) functional MT, MnSOD and/or γ-GTP activity. Human transcripts of the proteins are observed in the transfected tissue; SDS-PAGE and autoradiography of protein samples from biopsied tissue reveal de novo expression of a 6,000 dalton human MT, a 16,000 to 19,000 dalton human MnSOD, and a 62,000 dalton human γ-GTP. No expression is observed in mice that received a solution of naked DNA.

EXAMPLE 3

Preparation of MT, MnSOD and/or γ-GTP lipid carrier-nucleic acid complexes

Lipid carrier-nucleic acid complexes are prepared by methods well known in the art, such as those disclosed by Debs et al., WO93/12756 or Stribling et al., supra, the entire contents of which is incorporated by reference herein. Alternatively, liposomes for lipofection can be produced as follows or purchased from GIBCO BRL. To prepare liposomes for lipofection, 20 mg of egg phosphatrolycholine is rotary evaporated with a vacuum drier from a chloroform solution to form a thin film on the walls of a 5 ml round-bottomed flask for 1 hour. The dried thin film lipid is suspended in 0.5 ml phosphate buffered saline (PBS) pH 7.4 on a vortex mixer and then sonicated.

An expression vector comprising DNA encoding MT, MnSOD and/or γ-GTP and a promoter, such as human beta-actin promoter in pHB APr-1 is entrapped in the sonicated liposome suspension by extensively vortexing 0.5 ml of DNA solution with the sonicated suspension for 1 minute followed by three cycles of freezing and thawing. DNA-entrapped liposomes are separated from the non-entrapped DNA by gel filtration on a Sepharose 4B column diluted with PBS.

The amount of liposomes (30–40 μg) and the amount of DNA (1 to 5 μg) is optimized for cell type based on a dose response curve to determine cell toxicity. Felgner et al., (1989) supra. The amount of liposome used for lipofection is about 50% of its toxic concentration.

To prepare plasmid/cationic liposome complexes, cationic liposomes are made containing cationic lipid preparation of 1:1 DOTMA/DOPE (i.e. 1:1 of N-[1-(2,3-dioleyloxy)propyl]-N,N,N-triethylammonium (DOTMA) and dioleoyl phosphatidylethanolamine (DOPE). Stock solutions of lipids are dissolved in chloroform and stored under argon at −20° C. Lipids are mixed in round bottomed flasks and evaporated to dryness on a rotary evaporator under reduced pressure. Final lipid concentrations of 10 mM each are made by adding double-distilled water. The resulting mixture is sonicated for about 20 minutes. Between 5 and 50 mg, preferably 12 mg of plasmid is complexed to between 5 and 100 μmol, preferably 24 μmol of DOTMA/DOPE liposomes. LacZ plasmid/liposome complexes are prepared as controls.

EXAMPLE 4

In vivo expression of MT, MnSOD and/or γ-GTP following lipofection with plasmid/liposome complexes Mice are transfected using lipofection with DNA encoding MT, MnSOD, γ-GTP, or LacZ plasmid/liposome complexes prepared according to Example 3. Adult C3H/HeNsd mice of approximately 12 weeks of age are injected with the plasmid/liposome complex by passing a tube attached to a 28 gage needle through the oral cavity and depositing 150 µl of plasmid/liposome complex comprising 1 mg of either MT, MnSOD, γ-GTP, or LacZ plasmid DNA (10 µg/ml), and 56 µl of lipofectant at the top of the esophagus. A solution of naked-DNA, at the same concentration as that used in the liposome preparation, serves as a control.

The mice are sacrificed 24 hours later, and the esophagus removed. The tissue is tested for: (1) immunoreactive MT, MnSOD, or γ-GTP, as measured by immunoprecipitation or Western blotting, or LacZ, as measured by staining, and (2) functional MT, MnSOD and/or γ-GTP activity. Human transcripts of the proteins are observed in the transfected tissue; SDS-PAGE and autoradiography of protein samples from biopsied tissue reveal de novo expression of a 6,000 dalton human MT, a 16,000 to 19,000 dalton human MnSOD, and a 62,000 dalton human γ-GTP. LacZ expression is confirmed in mice that received LacZ plasmid/liposome complexes. No expression is observed in mice that received a solution of naked DNA.

EXAMPLE 5

Protection of esophagus from ionizing radiation and alkylating agents

Control mice and mice that transiently express recombinant MT, MnSOD, γ-GTP or a combination of these proteins in esophageal tissue, as a result of lipofection with plasmid/liposome complexes according to Example 4, are tested to see whether the recombinant protein(s) protect the esophagus during irradiation. A first group of mice is exposed to ionizing radiation to the lung with a dose of hemi-body irradiation delivering about 1800 to 2500 cGY in one fraction or about 2000 to 3000 cGY in multiple fractions. These regimens produce acute radiation esophagitis in unprotected animals within two to three days of the single fraction delivery. At serial time points after irradiation between about one day and two weeks after irradiation, the animals are sacrificed, and the irradiated and control esophagus are removed.

The effect of transgene expression on the development of chemoradiation-induced esophagitis also is assessed. A second group of mice is exposed to a chemoradiation treatment using taxol, to determine whether increased expression of MT, MnSOD and/or γ-GTP protects against the development of esophagitis resulting from chemoradiation therapy. In this case, the mice receive a single dose of 6 mg/kg taxol or a fractionated dose of 1.5 mg/kg/day over 5 days of taxol via intraperitoneal injection. On the last day of taxol injection, the experimental mice receive an esophageal injection of MT, MnSOD or γ-GTP plasmid/liposome complex. Control and experimental mice are irradiated with 1500, 1750 or 2000 cGy.

A mouse model for irradiation-induced esophagitis has been described previously. Rozenzweig et al., *Nucl. Med. Biol.*, 21: 171–178 (1994). According to the model, LD50/30 was used to describe mortality with deaths due to esophagitis occurring within the first 30 days following irradiation. C3H/HeJ mice were shown to have LD50/30 of 1900 cGy, which was decreased to 1252 or 1686 cGy when adriamycin was administered 1 or 7 days in advance, respectively.

The mouse model for esophagitis is used to assess mortality from esophagitis caused by radiation-induced changes, by comparing LD50/30 in control and experimental mice. In order to determine LD50/30, mice are irradiated 24 hours after injection with plasmid/liposome complex with a single dose of irradiation ranging from 1800 to 2500 cGy. The mice are shielded such that the irradiation is restricted to the pulmonary cavity. The mice are weighed before irradiation, and at 7, 14, 21 and 28 days after irradiation. The mice are observed daily and are sacrificed if they lose more than 20% of their body weight or experience difficulty breathing or moving. After 30, days, all the remaining mice are sacrificed.

A fractionated irradiation schedule also is used. In this case, the mice receive an intraesophageal injection of plasmid/liposome complex 24 hours before the first dose and every 48 hours thereafter. The irradiation dose is fractionated as 400 cGy×5, 300 cGy×10, or 250 cGy×12.

Esophagitis also is monitored by following its histological progression. Mice are sacrificed at serial points following treatment, and the esophagus is removed, fixed in formalin, sectioned and stained it with hematoxylin and eosin. The sections are examined under a microscope for alterations in the mucosal layer, which are scored using Optimas Image Analysis software to quantitate damage to the esophagus.

Values for LD50/30 are significantly lower in mice that receive intraesophageal injections of plasmid/liposome complex that contains MT, MnSOD or γ-GTP. In addition, histological examination of the esophagus demonstrates that the complexes effectively prevent the damage to the mucosal layer that is associated with irradiation-induced esophagitis.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

What is claimed is:

1. A method for protecting cells of the oral cavity, oropharynx, esophagus, small intestine or colon in a mammalian subject from an agent that elicits production of a toxic species selected from the group consisting of a free radical, a superoxide anion, and a heavy metal cation, said method comprising administering in vivo, to normal cells of the oral cavity, oropharynx, esophagus, small intestine or colon at a site remote from a site to be treated by said agent, a protective pharmaceutical composition to the oral cavity, oropharynx, or esophagus of a subject undergoing radiation treatment for lung cancer, or to the small intestine or colon of a subject undergoing radiation treatment for cancer in the lower abdomen, said pharmaceutical composition comprising (A) a polynucleotide that encodes a protein that is transiently expressed in said subject, and wherein said protein neutralizes or eliminates said toxic species; and (B) a pharmaceutically acceptable vehicle for said polynucleotide.

2. The method of claim 1, wherein said agent is ionizing radiation.

3. The method of claim 2, wherein said ionizing radiation is clinical radiation therapy.

4. A method as claimed in claim 2, wherein said vehicle is an adenovirus vector or a liposome and said protein is selected from the group consisting of gamma glutamyl transpeptidase, manganese superoxide dismutase, and metallothionein.

5. The method of claim 1, wherein said agent is a chemotherapeutic drug.

6. The method of claim 1, wherein said polynucleotide is a cDNA and said vehicle is a liposome.

7. The method of claim 1, wherein said polynucleotide is a cDNA and said vehicle is an adenovirus vector.

8. The method of claim 1, wherein said protein is selected from the group consisting of gamma glutamyl transpeptidase, manganese superoxide dismutase, and metallothionein.

9. A method as claimed in claim 8 wherein said vehicle is an adenovirus vector or a liposome.

10. The method as claimed in claim 9 which is a method of protecting the oral cavity, oropharynx, esophagus, small intestine or colon.

11. The method of claim 1, wherein said protein is gamma glutamyl transpeptidase.

12. The method of claim 1, wherein said protein is manganese superoxide dismutase.

13. The method of claim 1, wherein said protein is metallothionein.

14. The method of claim 1, wherein said pharmaceutical composition comprises a mixture of polynucleotides selected from the group consisting of a polynucleotide encoding gamma glutamyl transpeptidase, a polynucleotide encoding manganese superoxide dismutase and a polynucleotide encoding metallothionein.

15. The method of claim 1, wherein said polynucleotide is under control of an inducible transcriptional regulatory sequence.

16. The method of claim 1, wherein said polynucleotide is under control of a radio inducible transcriptional regulatory sequence.

17. The method of claim 1, wherein said subject is a lung cancer patient requiring protection of tissues of the oral cavity, oropharynx, and esophagus.

18. The method of claim 1, wherein said subject is a patient, with cancer in the lower abdomen, requiring protection of tissues of the colon and small intestine.

19. The method of claim 18, wherein said cancer is cervical cancer.

20. The method of claim 18, wherein said cancer is prostate cancer.

21. The method of claim 18, wherein said cancer is endometrial cancer.

22. The method of claim 18, wherein said cancer is ovarian cancer.

23. The method of claim 18, wherein said cancer is bladder cancer.

* * * * *